United States Patent [19]

Lash

[11] Patent Number: 4,995,410
[45] Date of Patent: Feb. 26, 1991

[54] OSTOMY CLEANING AND RECEPTACLE REPLACEMENT STATION

[76] Inventor: Richard L. Lash, P.O. Box 8, Montpelier, Id. 83254

[21] Appl. No.: 462,644

[22] Filed: Jan. 9, 1990

[51] Int. Cl.⁵ .................... B08B 3/02; B08B 13/00
[52] U.S. Cl. .................................. 134/113; 4/665; 134/115 R; 134/115 G
[58] Field of Search ............... 134/113, 115 R, 115 G, 134/172, 198; 4/665; 312/228, 246, 248

[56] References Cited

U.S. PATENT DOCUMENTS

| | | | |
|---|---|---|---|
| 125,991 | 4/1872 | Schneemann | 312/228 |
| 413,200 | 10/1889 | Milligan | 312/248 X |
| 1,263,384 | 4/1918 | De Labaume | 312/228 X |
| 1,724,479 | 8/1929 | Havener | 312/228 X |
| 2,058,967 | 10/1936 | Emmons | 4/665 |
| 2,223,566 | 12/1940 | Koch | 604/277 |
| 2,595,009 | 4/1952 | Sillen | 4/665 |
| 2,860,348 | 11/1958 | McClenahan | 4/665 |
| 4,194,506 | 3/1980 | Voorhies | 604/334 |
| 4,257,680 | 3/1981 | Baczkowski | 128/21 X |
| 4,668,227 | 5/1987 | Kay | 134/57 R X |
| 4,692,159 | 9/1987 | Kuzemchak | 604/277 |

Primary Examiner—Philip R. Coe
Attorney, Agent, or Firm—Trask, Britt & Rossa

[57] ABSTRACT

A cleaning station for storing, cleaning and replacing ostomy equipment. The station is mountable on a wall and is further adapted to be positioned over or in close proximity to a toilet. The cleaning station includes a cabinet, a countertop and sink, and a support adapted to support the cabinet on a wall. The sink is fitted with a drain conduit adapted for discharging waste from the sink to a disposal site. The support is adapted to extend laterally whereby the cabinet may be displaced outwardly from its position adjacent a wall to a location above a waste disposal site such as a conventional toilet.

21 Claims, 20 Drawing Sheets

OSTOMY CLEANING AND RECEPTACLE REPLACEMENT STATION

BACKGROUND OF THE INVENTION

This application is related to pending U.S. Pat. application Ser. No. 358,181, filed May 25, 1989.

1. Field of Invention

This invention relates to sanitation and personal health care equipment. More particularly, the invention is directed to equipment adapted for use by persons who have had a colostomy, urostomy, or other similar surgical procedure which produces a new bodily opening, or stoma, adapted for excretory functions.

2. State of the Art

Following ostomy surgery, an ostomy patient must wear a pouch or bag which is configured to cover the surgically created stoma or opening. Typically, the stoma is created in the general area of the abdomen. The bag is kept in place about the stoma by means of a belt worn around the patient's abdomen or waist. Due to the nature of their function and operation, ostomy bags must be periodically removed from the user and cleaned. After cleaning, the bag is subsequently reattached to the user. The removal, cleaning and reattachment operations are typically performed several times each day by an ostomy patient.

Recognizably, the cleaning of an ostomy bag requires considerable care in order to avoid the soiling and contamination of the individual cleaning the bag. Furthermore, contamination of the immediate environment surrounding the cleaning site is of concern. It is a matter of considerable importance that the waste materials be emptied from the bag efficiently and sanitarily and thereafter be directed to a waste disposal site without any undue contamination of either the individual cleaning the bag or the environment around the individual. A number of devices have been developed for assisting in the cleaning of ostomy bags. These devices generally include a specialized nozzle connected to a hose. The hose, in turn, is connected to a water source. Representative devices are disclosed in U.S. Pat. No. 4,194,506 (Voorhies), U.S. Pat. No. 2,223,563 (Koch), and U.S. Pat. No. 4,692,159 (Kuzemchak). A cleansing apparatus is also disclosed in U.S. Pat. No. 4,668,227 (Kay). Few, if any, of the foregoing ostomy cleaning devices have specifically addressed the problem of disposing of the waste material which is emptied or flushed from the ostomy bag. Furthermore, prior cleaning devices generally have not focused on the visibility problems encountered by many ostomy patients during the removal and replacement of their ostomy equipment. These problems are known to be specifically acute when the stoma is located in a difficult area for the patient to see, or when the patient's ability to see the stoma is hampered by other physical disabilities the patient may have.

It would be very advantageous, therefore, to have an integrated means for assisting the ostomy patient removing, cleaning and replacing ostomy equipment. In addition, these means should be adapted for disposing of waste materials, emptied from the ostomy bag, and for conveniently storing cleaning and replacement equipment.

SUMMARY OF THE INVENTION

The instant invention is a work station which assists an ostomy patient in removing, replacing and cleaning an ostomy bag and its associated equipment. The station may further include space for storage of such associated components.

Generally, the station comprises frame means for retaining the components required by the ostomate.

One of the components is a mirror for assisting the user in viewing his body. The mirror is positioned generally parallel to the user's body to enhance the user's view of the ostomy, thereby facilitating the user's ready removal, cleaning and replacement of the ostomy bag. Thus, the user has a clear view of the ostomy bag in the mirror, even when the bag is attached to the ostomy. Cleaning and manipulation of the bag is easier and more certain.

The frame means may also include a generally horizontal countertop upon which an ostomy bag may be placed and retained while cleaning.

The countertop has a sink formed therein to allow liquid and waste materials from an ostomy bag to drain from the countertop. The countertop is sloped slightly downward toward the sink to enhance draining.

The sink drains into an outlet conduit which carries away waste materials and fluid into a toilet bowl or other means for disposal.

A fluid-carrying, flexible hose terminating in a controllable spray head may be mounted in the station for washing the ostomy and the ostomy bag and associated ostomy equipment. The hose is retractable into the frame means and is normally connected to a pressurized fluid source such as a municipal or household water supply line.

Other components which may be incorporated in the frame means include a water or germicide reservoir, a pump for delivering water to the spray head, a macerator for reducing the particle size of solid waste materials, lighting means, deodorizing means, and other toiletry appliance and articles.

The frame means of this invention may comprise a single cabinet unit containing all of the components. The cabinet may be mounted to any wall in close proximity to a toilet. In one embodiment, the cabinet can be movably positioned above the toilet to facilitate emptying of the waste materials into the toilet. In the wall-mounted embodiment, stabilizing arms extend downwardly from the bottom of the cabinet and lockingly engage with the seat or rim of the toilet. In an alternative embodiment, the cabinet is connected to legs with rollers and may be rolled into place above a toilet. The ability to position the cabinet above a toilet provides a unique and convenient means for cleaning ostomy equipment and for disposing of the eliminated waste.

The frame means may also comprise two separated units. A portable lower unit houses the countertop, sink, spray arrangement and mirror, and is designed to rest upon the upper surface of a toilet bowl and circumscribe it. A permanently mounted upper unit comprises a cabinet which includes storage space for ostomy components, an additional mirror, lighting means, and other optional items, all of which are used in unison with the lower unit for rapid and convenient use by the ostomate. The outward appearance of the cabinet disguises its primary use, and the lower unit is easily stored in a closet or other area.

These features and others are more clearly described in the following description of the preferred embodiments in conjunction with the drawings and claims.

DETAILED DESCRIPTION OF THE ILLUSTRATED EMBODIMENTS

Figure 1:
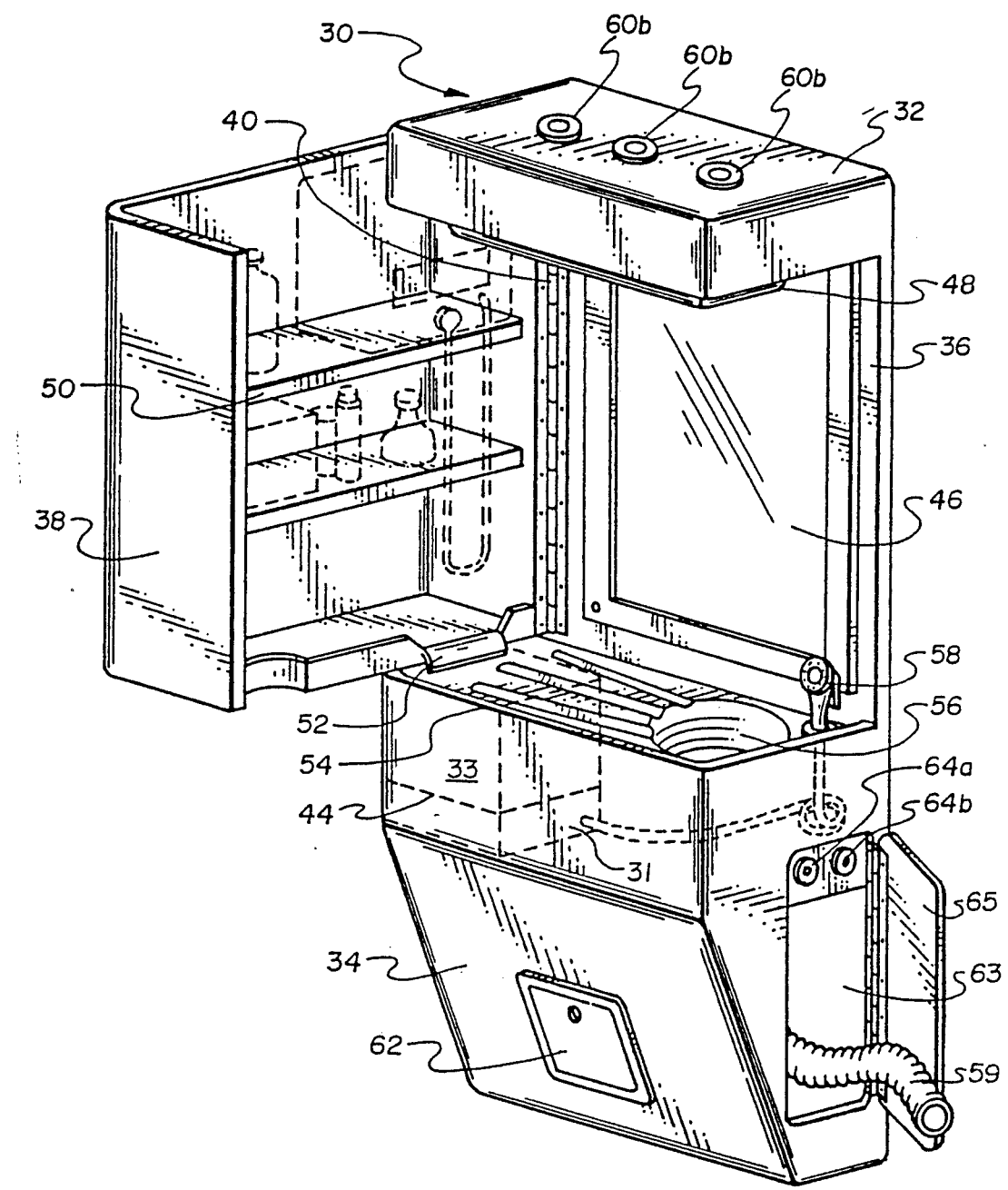
FIG. 1 is an elevational perspective view of the station cabinet according to the present invention.
Figure 2:
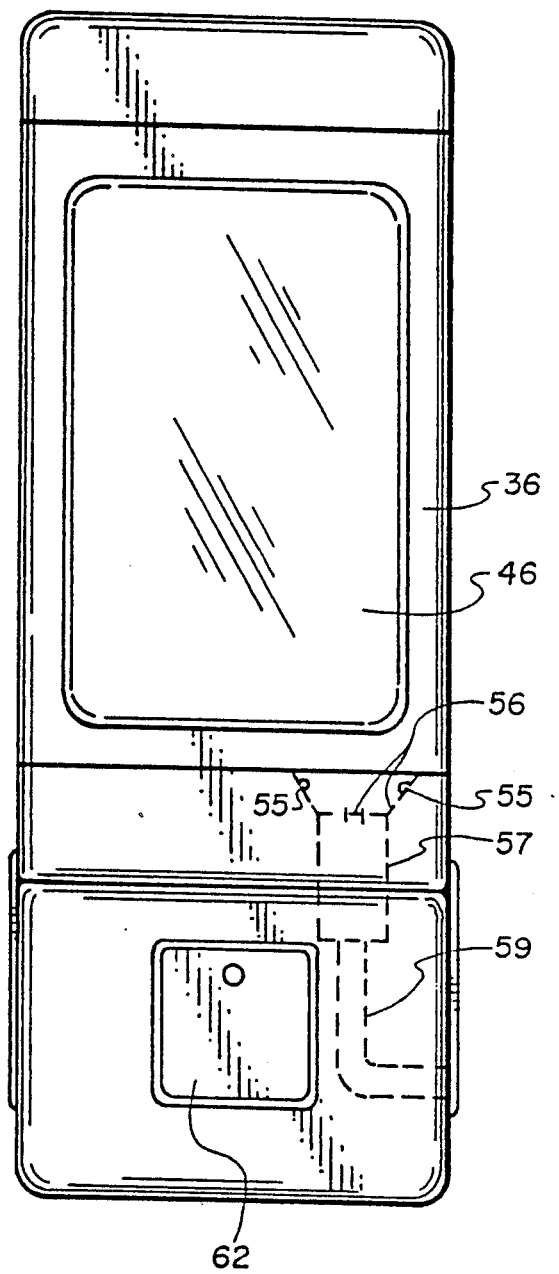
FIG. 2 is a front view of the station cabinet.
Figure 5:
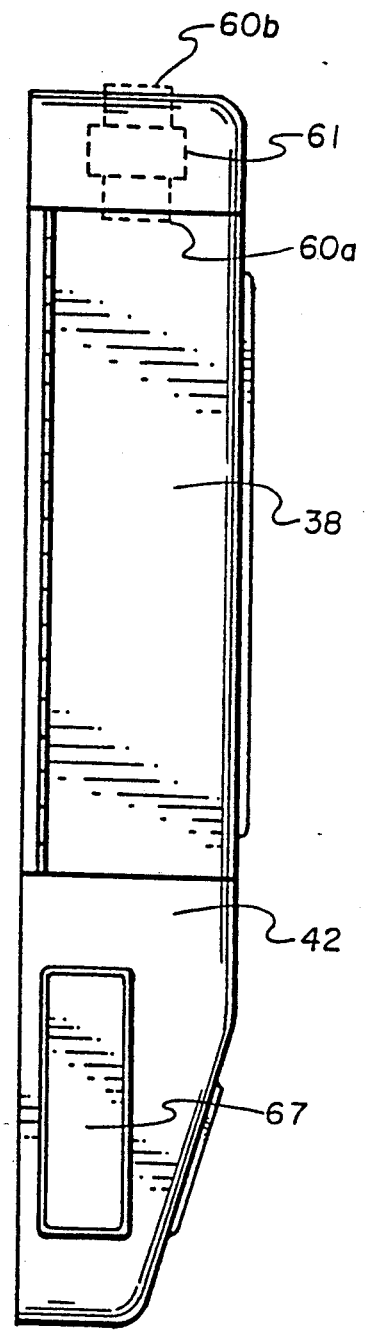
FIG. 5 is a view of the left side of the station cabinet.
Figure 6:
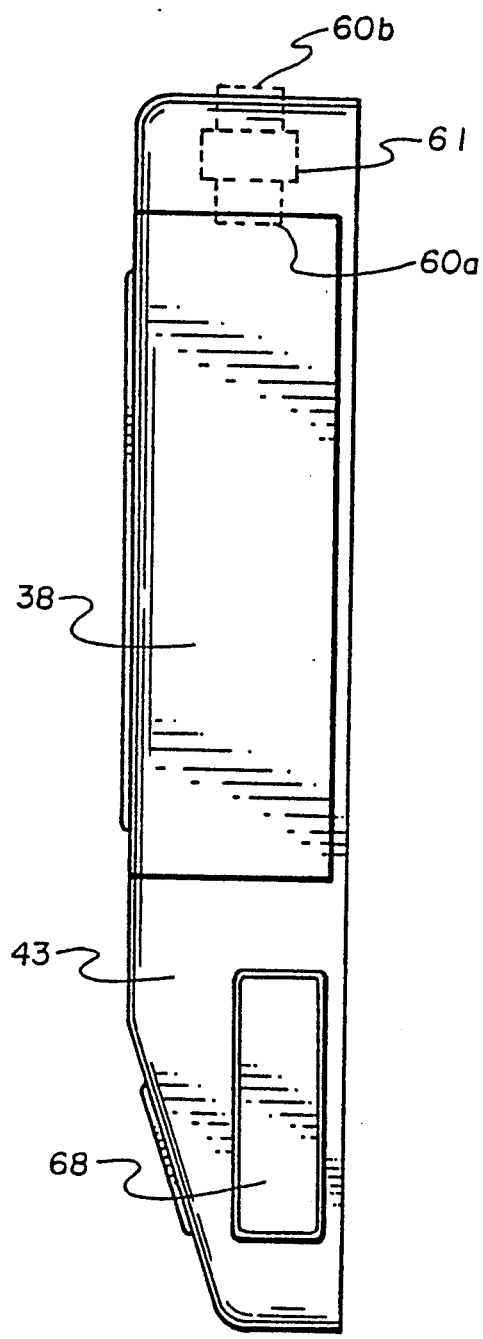
FIG. 6 is a view of the right side of the station cabinet.
Figure 7:
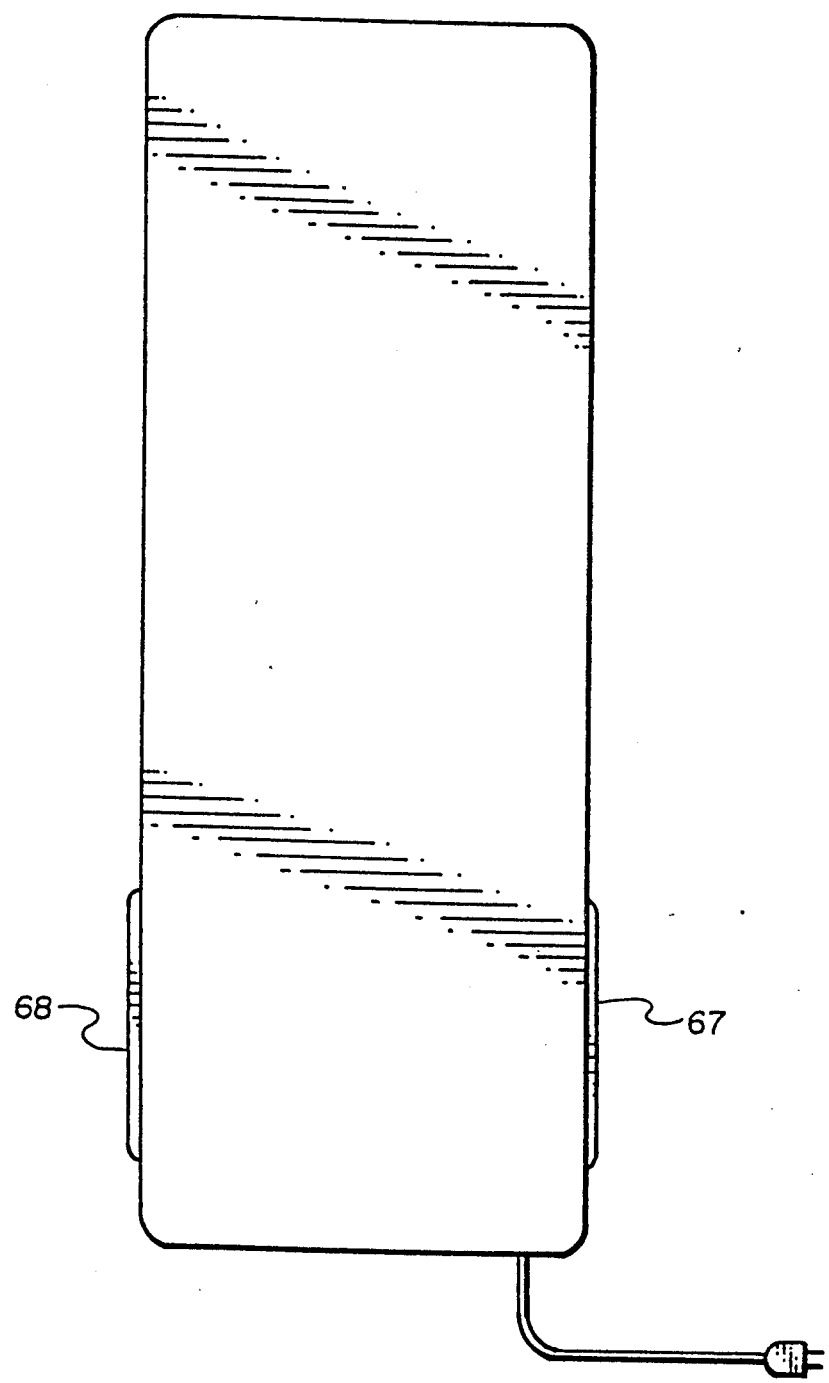
FIG. 7 is a view of the back side of the station cabinet.
Figure 8:
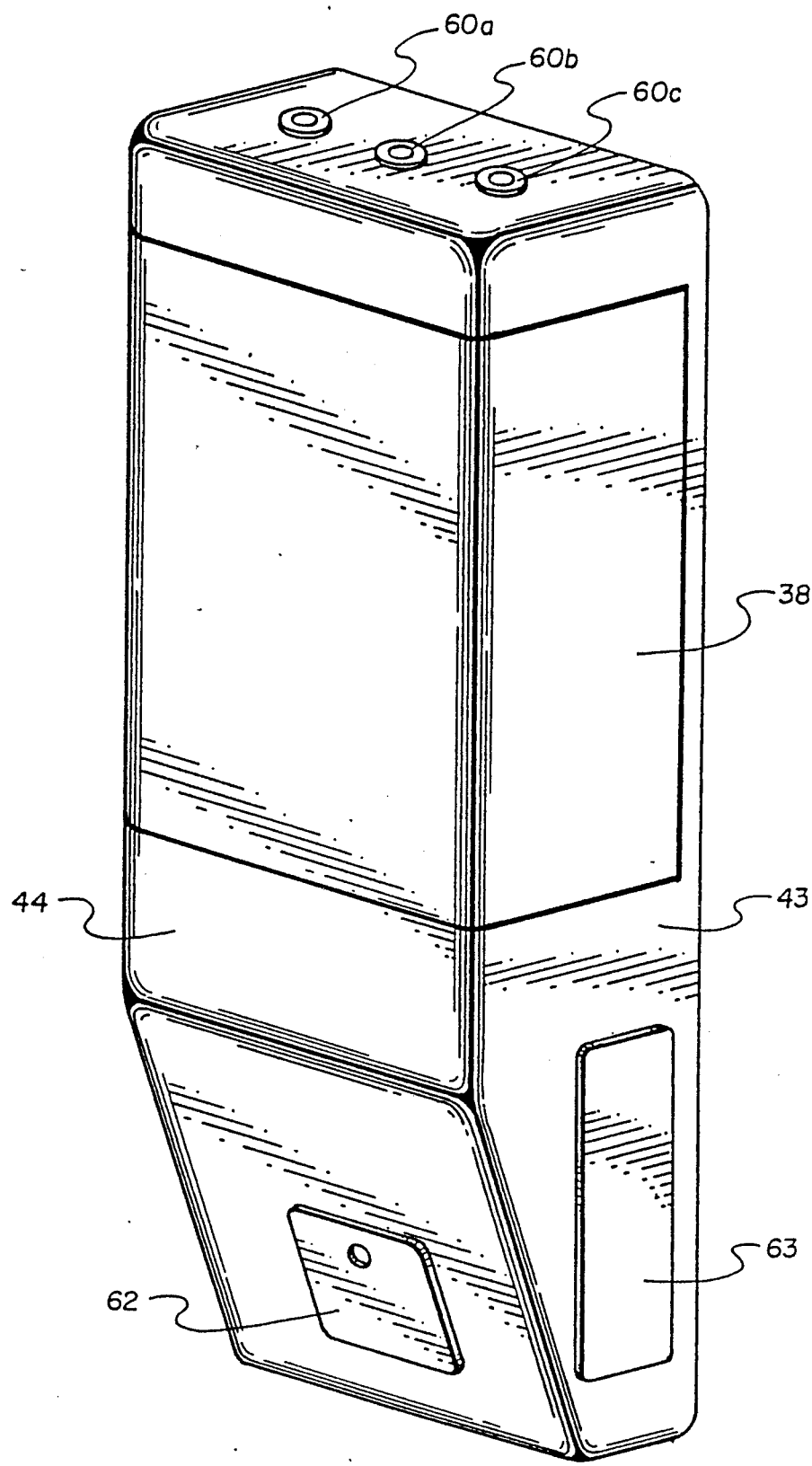
FIG. 8 is an elevational perspective view of the station cabinet with the cabinet door in the closed position.

One embodiment of the invention, as depicted in FIG. 1, includes a cabinet, generally 30, with a top portion 32, a bottom portion 34, and a back wall 36. In the particular embodiment illustrated in FIG. 1, the cabinet 30 includes a door 38. The door is joined to the back wall 36 of the cabinet by hinge 40. When in the closed position, the door 38 engages with the sides 42, 43 and front wall 44 of the cabinet, as illustrated in FIGS. 5, 6, and 8. As illustrated in FIG. 2, the cabinet may be constructed without a door, thereby leaving the back wall 36 exposed.

A mirror 46 is placed on the back wall 36 of the cabinet 30 and allows the ostomate to view his abdominal area during the removal and replacement of the ostomy bag or other associated equipment. Referring again to FIG. 1, a light source 48 is located in the upper portion 32 of the cabinet. The light may typically be a lightbulb recessed into the upper portion 32 of the cabinet and may be covered with a translucent cover. The door 38 is constructed with shelves 50 upon which equipment or supplies can be kept. The door is further constructed with a downwardly sloping lip 52 (FIG. 1) mounted on its lower edge. The lip 52 restricts the angle of opening of the door.

The lip 52 is positioned such that as the door 38 is rotated about its hinge 40 into a closed orientation, the lip passes over the surface of the countertop 54 sufficiently close thereto that waste materials resting on that countertop are swept off of the countertop and directed into a sink 55 mounted within the countertop 54.

The bottom portion 34 of the cabinet is formed with an upwardly facing surface or countertop 54 upon which an ostomy bag or other equipment may be placed for washing. The countertop is slightly angled downwardly toward a sink 56. Cleaning of the ostomy bag is accomplished by means of water or other fluid ejected from a spray nozzle 58 which is connected to a retractable hose (shown in phantom). Water may be delivered through the hose by means of a pump 31 housed internally within the bottom portion 34. Water is preferably obtained by connecting a hose to an external water supply, such as the water supply of a bathroom sink or the water supply of a toilet. Alternatively, cleaning fluid or water may be pumped from a reservoir 33 which may be housed within the bottom portion 34 of the cabinet.

Water and waste materials which are flushed out of the ostomy bag drain from the angled countertop 54 into the drain 56. The waste material and runoff may then pass through an electrically-powered macerating device 57 (e.g. a garbage disposal) connected to the drain, and the solid waste material can then be processed to a more toilet-flushable form. The waste material then passes into a flexible drain conduit 59 which is positioned by the user above or in the bowl of a toilet. The waste drains from the sink through the conduit 59 under the force of gravity. In addition, spray heads 55 connected to a source of pressurized water may be placed within the sink 56 to rinse the sink by a swirling spray or flow of water.

Figure 3:
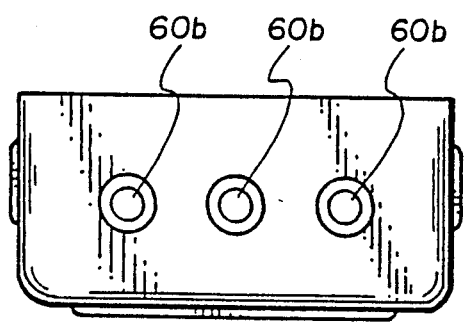
FIG. 3 is a top view of the station cabinet.
Figure 4:
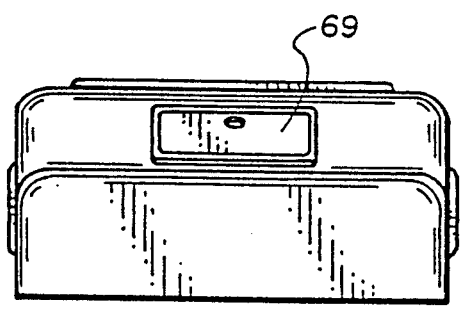
FIG. 4 is a bottom view of the station cabinet.

The upper portion 32 of the cabinet has electrically powered exhaust fans 60a and vents 60b mounted therein. The fans 60a aid in drawing off from the area above the countertop 54 the malodorous smell associated with fecal matter. A filter 61 comprising activated carbon or other adsorbent is located in front of or behind light source 48, to remove odors from air drawn from the cleaning area. The vents 60b can be more clearly seen in FIGS. 3 and 8. The upper portion of the cabinet 30 may be constructed so as to provide a storage area for equipment or supplies.

The bottom portion 34 of the cabinet has various access ports 62, 63 through which the components housed therewithin may be reached for inspection, repair, cleaning or refilling. Each of the access ports 62, 63 may have a closeable door 65 mechanically associated therewith to cover the access. Referring specifically to FIG. 1, the access port 63 may also house dials or electrical switches 64A, 64B for actuating and/or controlling the electrical components therein, such as the pump and macerating device.

The cabinet is adapted to be positioned over or proximate toilet facilities. This positioning facilitates convenient disposal of the waste materials flushed from the ostomy bag and equipment. The invention shown in FIGS. 1-8 includes means for securely attaching the cabinet to a wall 47, behind or to the side of a toilet. In this embodiment, the flexible drainage pipe 59 is dimensioned sufficiently to permit the user to withdraw the free end of that pipe 59 through access port 63 and thereafter position it in the bowl of the toilet 27.

In alternative constructions, the cabinet 30 is adapted to be stored at a location spatially removed from the toilet 27. In these constructions, the cabinet 30 includes means for facilitating its movement from its storage location to a work situs over the toilet 27. One such alternative construction is illustrated in FIGS. 9-11.

Figure 9:
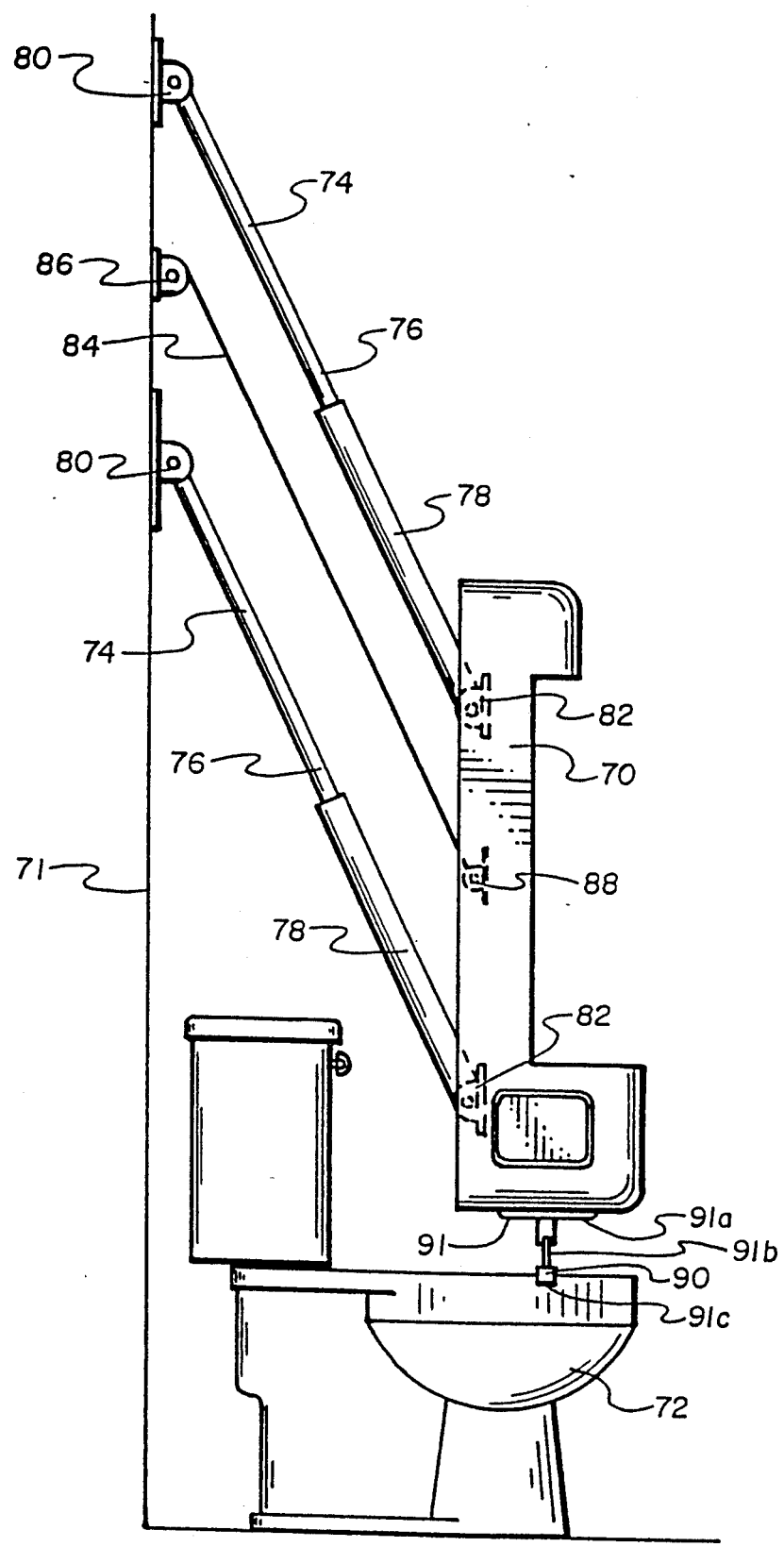
FIG. 9 is a side view of an embodiment for mounting the cabinet to a wall above a toilet using adjustable arms.
Figure 10:
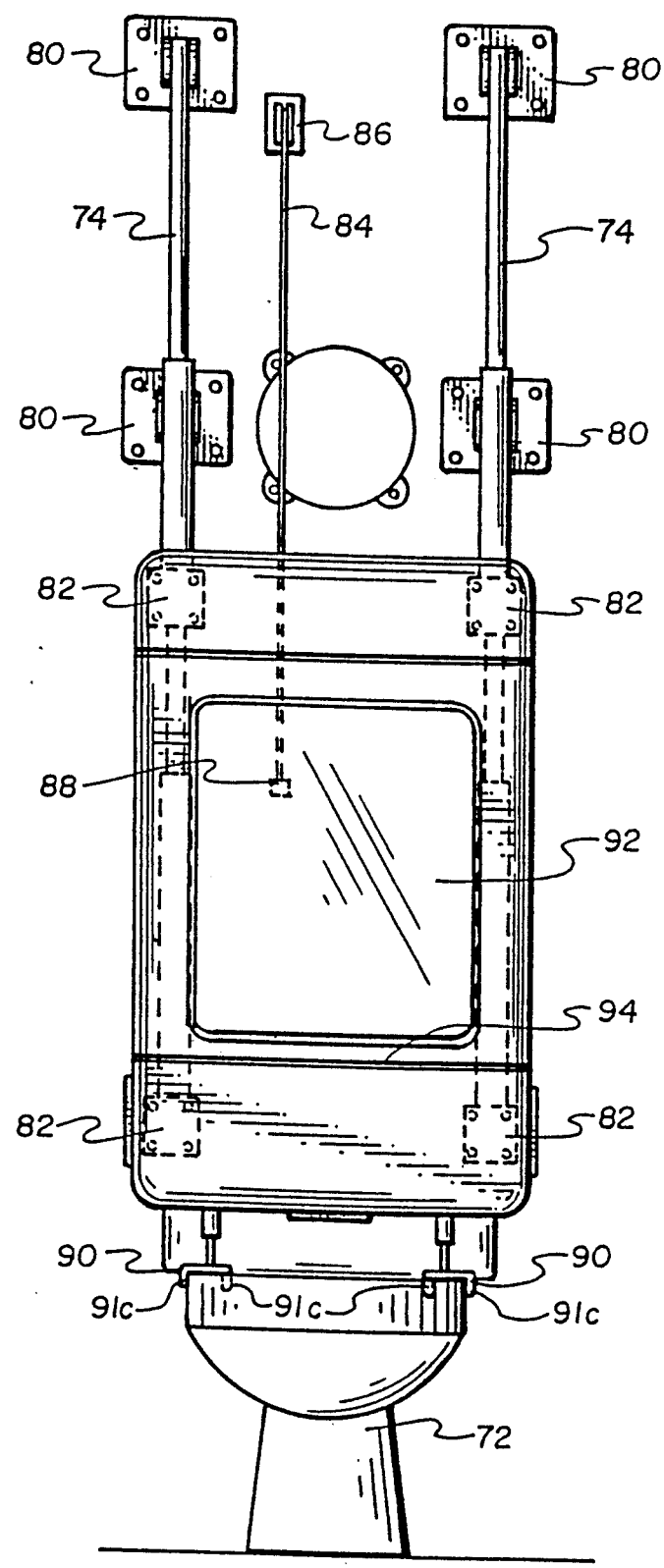
FIG. 10 is a front view of the cabinet mounted above a toilet using adjustable arms.
Figure 11:
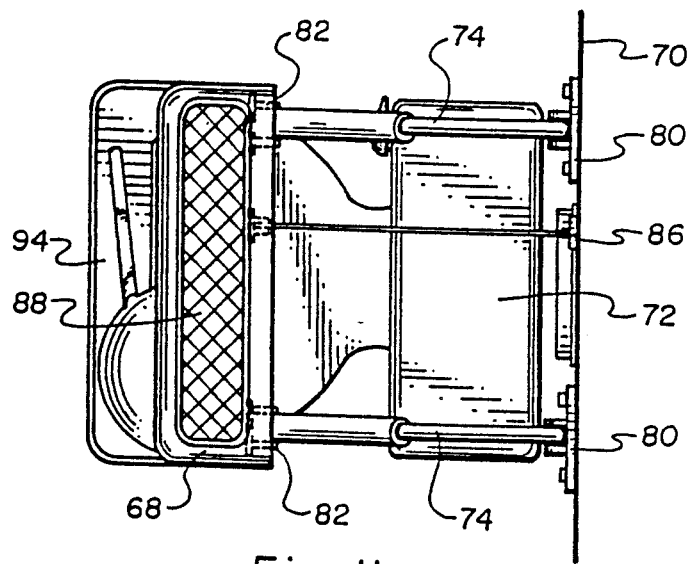
FIG. 11 is a top view of the cabinet mounted above a toilet using adjustable arms.

FIGS. 9, 10, and 11 illustrate an embodiment for attaching the cabinet to the wall 71 above a toilet 27 by means of pressurized fluid cylinder arms 74. Referring specifically to FIG. 9, each pressurized fluid cylinder arm 74 includes a rod 76 slidably disposed within a sleeve 78 which is filled with fluid, e.g. a pneumatic cylinder. One end of each rod 76 is securely and pivotally connected to a plate 80 mounted on the wall. The cylinder arms 74 are pivotally connected to the back 82 of the cabinet as shown in phantom in FIGS. 9, 10 and 11. The orientation of the cabinet relative to the to the wall and its position above the toilet 72 is controlled by a conventional cable 84 wound on a spring-loaded retractable reel 85. The cable 84 is connected at its end to the cabinet 70 and plate 86 positioned on the wall, and connected at the other end to the back 82 of cabinet 88.

After the cabinet is positioned over the toilet 72, the cabinet 70 can be secured in place vis-a-vis the toilet 72 by an adjustable clamp 90. The clamping arrangement 90 may include a pair of clamp units 91 spacedly mounted opposing sides of the cabinet 70. As shown, each clamp unit 91 may include a mounting bracket 91A which is secured to the bottom of the cabinet. The bracket 91A defines a female threaded aperture therein, through which is threaded a male threaded support shaft 91B. On the lower end of the support shaft 91B is mounted a "C"-clamp-like structure having a pair of spacedly positioned jaws 91C. The jaws 91C may be of a fixed or alternatively an adjustable construction. The "C"-clamp is configured to receive the rim 92 of the toilet bowl between its spacedly positioned jaws and form a secured union with that rim 92. In the adjustable "C"-clamp construction, one of the jaws includes a male threaded member threaded through a female aperture in the jaw. The threaded member may be displaced either toward or away form the opposing fixed jaw to thereby form a secured union with the rim which is positioned between the two jaws. When the cabinet is mounted above the toilet, the mirror 92 is oriented at approximately the waist level of the user, thereby allowing the user to view his abdominal area. Further, the countertop area 94 of the cabinet is positioned at an appropriate height for the user's manipulating the ostomy cleaning equipment. After use, the cabinet's securement to the toilet can be detached by either simply lifting the cabinet upwards sufficiently to disengage the clamp structure from the rim 92 or alternatively, threadingly disengaging the adjustable "C"-clamp structure and thereafter lifting the cabinet upwards sufficiently to disengage the clamp structure. The cable arrangement 84 can thus be actuated to return the cabinet to its stored position on the wall.

Figure 12:
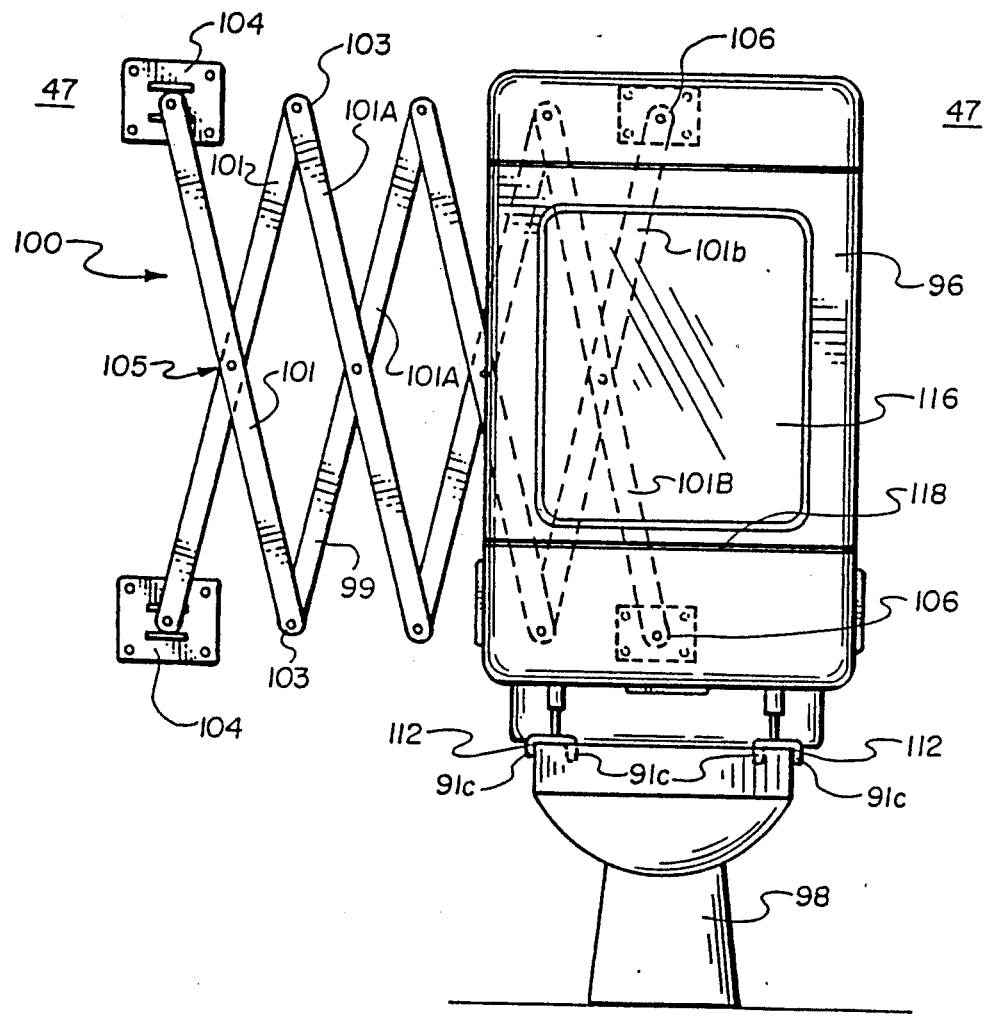
FIG. 12 is a front view of the cabinet mounted to a wall beside a toilet using adjustable "scissor" arms.
Figure 13:
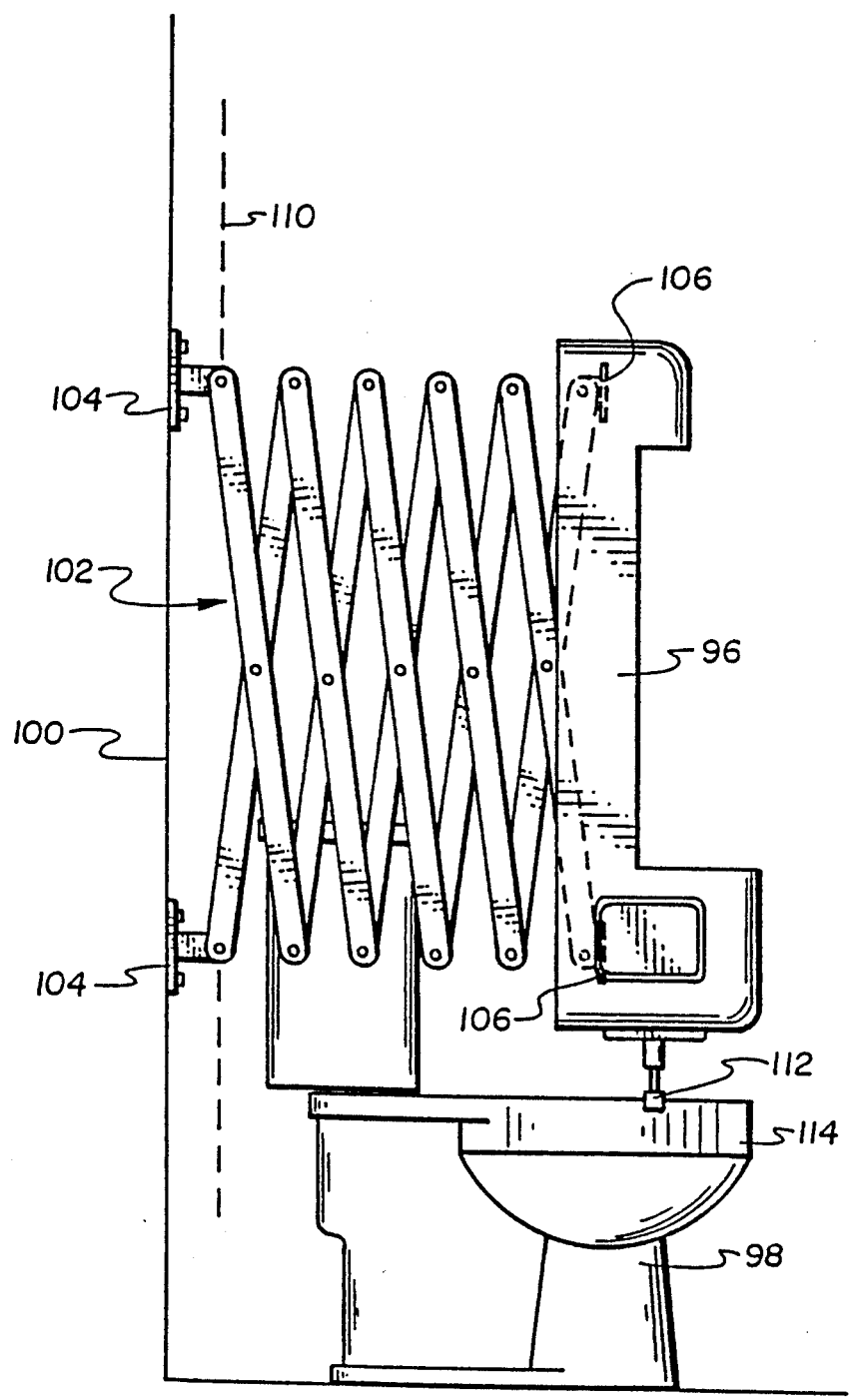
FIG. 13 is a side view of the cabinet mounted to a wall beside a toilet using adjustable "scissor" arms.
Figure 14:
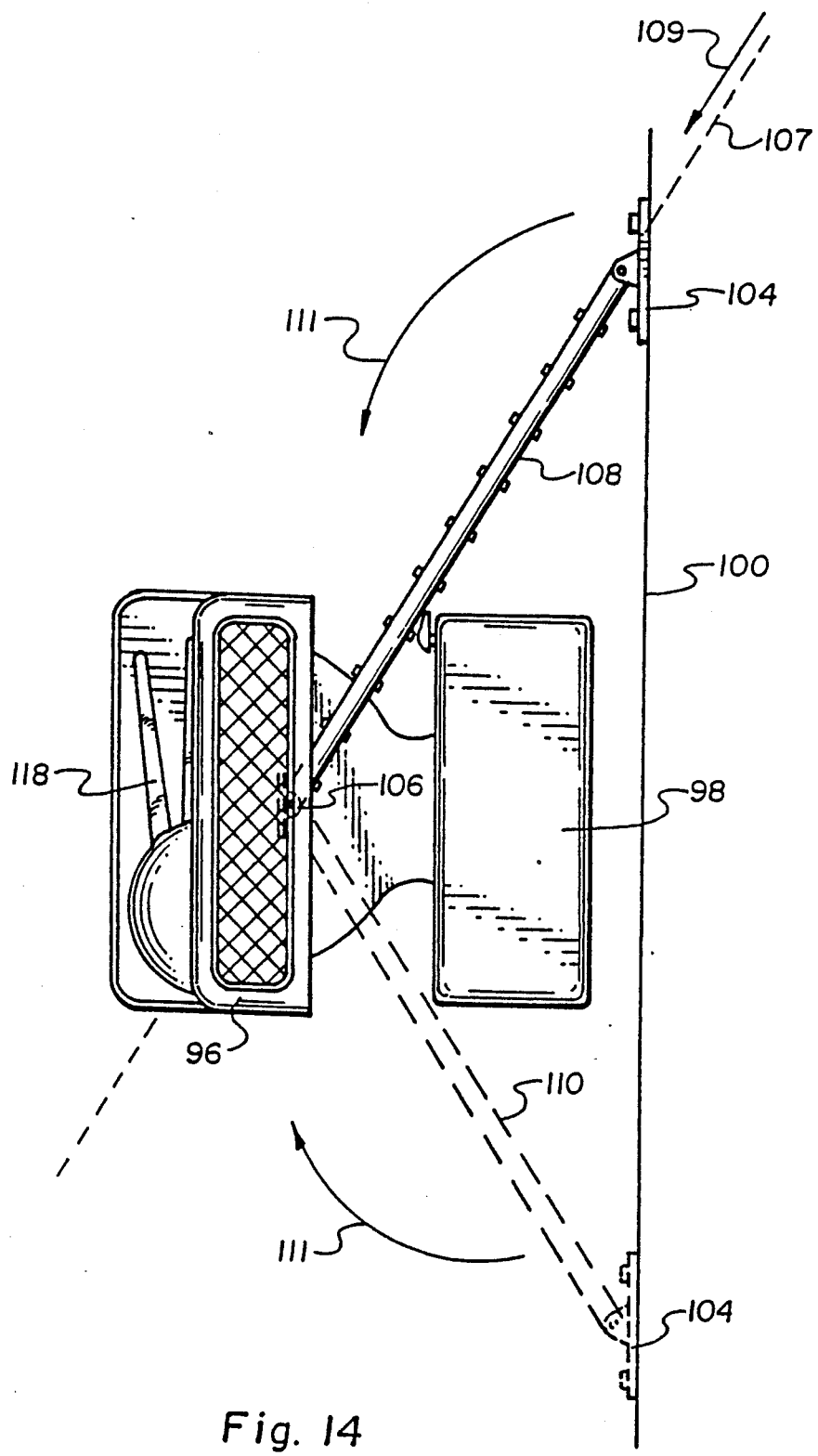
FIG. 14 is a top view of the cabinet illustrated as being mountable to a wall on either side of a toilet using adjustable "scissor" arms.

FIGS. 12, 13 and 14 illustrate an alternative embodiment of the cabinet, wherein the cabinet 96 is secured to a wall laterally from the toilet 98 and is rendered selectively positionable above the toilet 98 by a scissor-like extendible support mechanism 99. As shown, mechanism 99 includes a plurality of elongate linear members 101 which are arranged in pairs. Each pair of members 101 is pivotedly mounted to one another by a pin which extends through an aperture defined at approximately the midpoint of each member 101. Each pair of members 101 is pivotedly secured to a laterally positioned pair of members 101A at the free ends of the members 101. For example, as shown in FIG. 12, members 101 are pivotedly secured at their free ends 103 to the free ends of a laterally positioned second pair of members 101A by pins 105 which extend through apertures defined in those free ends.

The free ends 103 of the first pair of members 101 are each pivotedly mounted to respective mounting brackets 104 which are secured to the wall 47.

The various pairs of members 101 are arranged to extend laterally. The last pair of members, generally 101B are pivotedly mounted at their free ends to the back of the cabinet.

As shown to advantage in FIGS. 13 and 14, the mechanism 99 provides a means of displacing or extending the cabinet 96 linearly along the longitudinal axis 107 of the mechanism 99 as shown by arrow 109. Furthermore, the cabinet 96 may be rotated about the upright vertical axis 110 defined by the pivot mounting of the members 101 on the wall bracket 104, as shown by arrow 111. In this embodiment, the cabinet may be attached to either the left side of the toilet and be extended, i.e., displaced to the right, as illustrated in FIG. 12, or it can be mounted on the right side of the toilet 98 and displaced to the left as shown by FIG. 14.

The cabinet 96 can be secured into position above the toilet 98 by means of adjustable clamps 112 which engage with the rim 114 of the toilet 98, as previously illustrated in FIGS. 12 and 13. As with other embodiments, the position of the cabinet 96 relative to the toilet 98 allows the user to view himself in the mirror 116 and to have access to the countertop 118.

Figure 15:
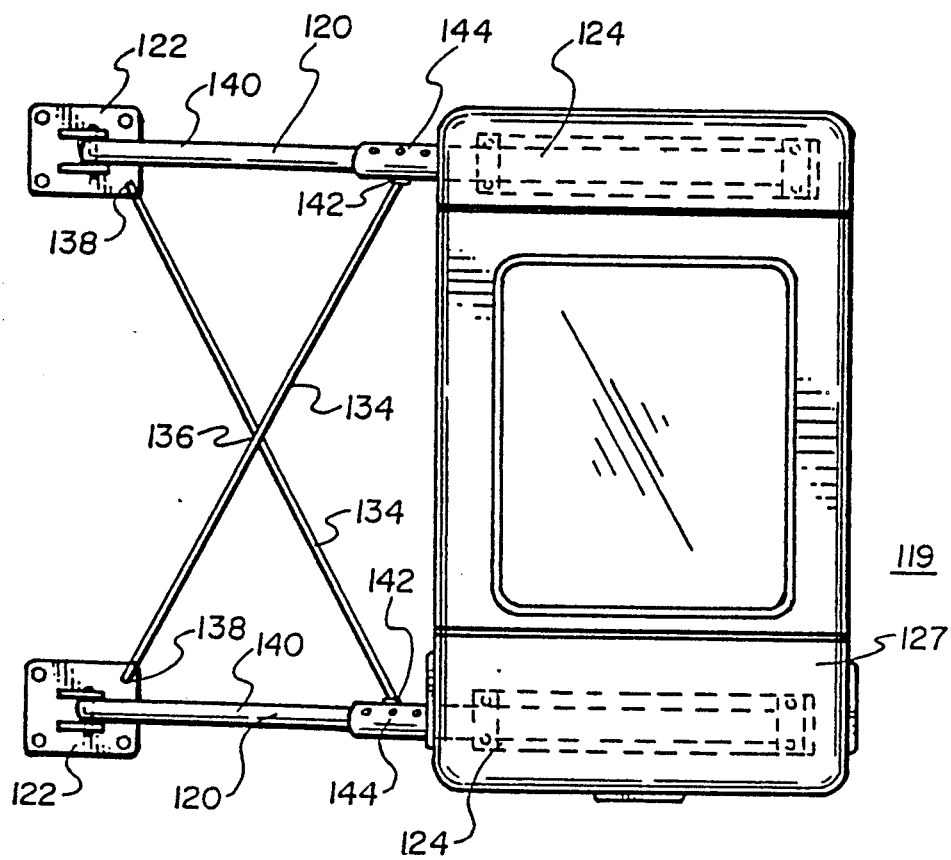
FIG. 15 is a front view of the cabinet mounted to a wall.
Figure 15:
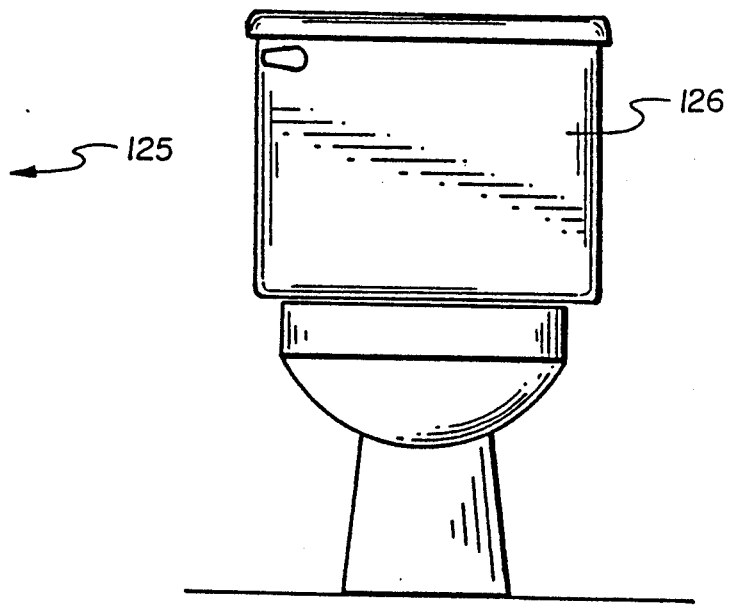
Figure 16:
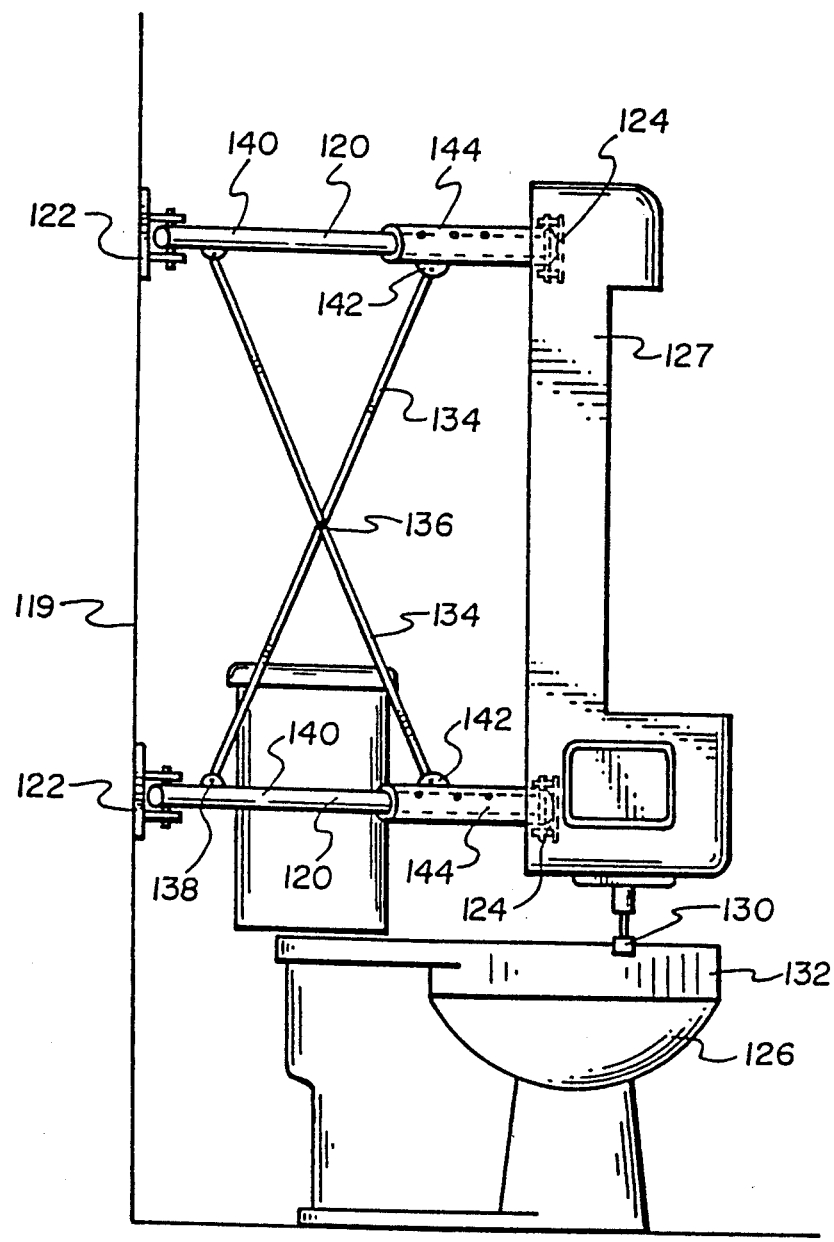
FIG. 16 is a side view of the cabinet mounted to a wall beside a toilet using adjustable arms.
Figure 17:
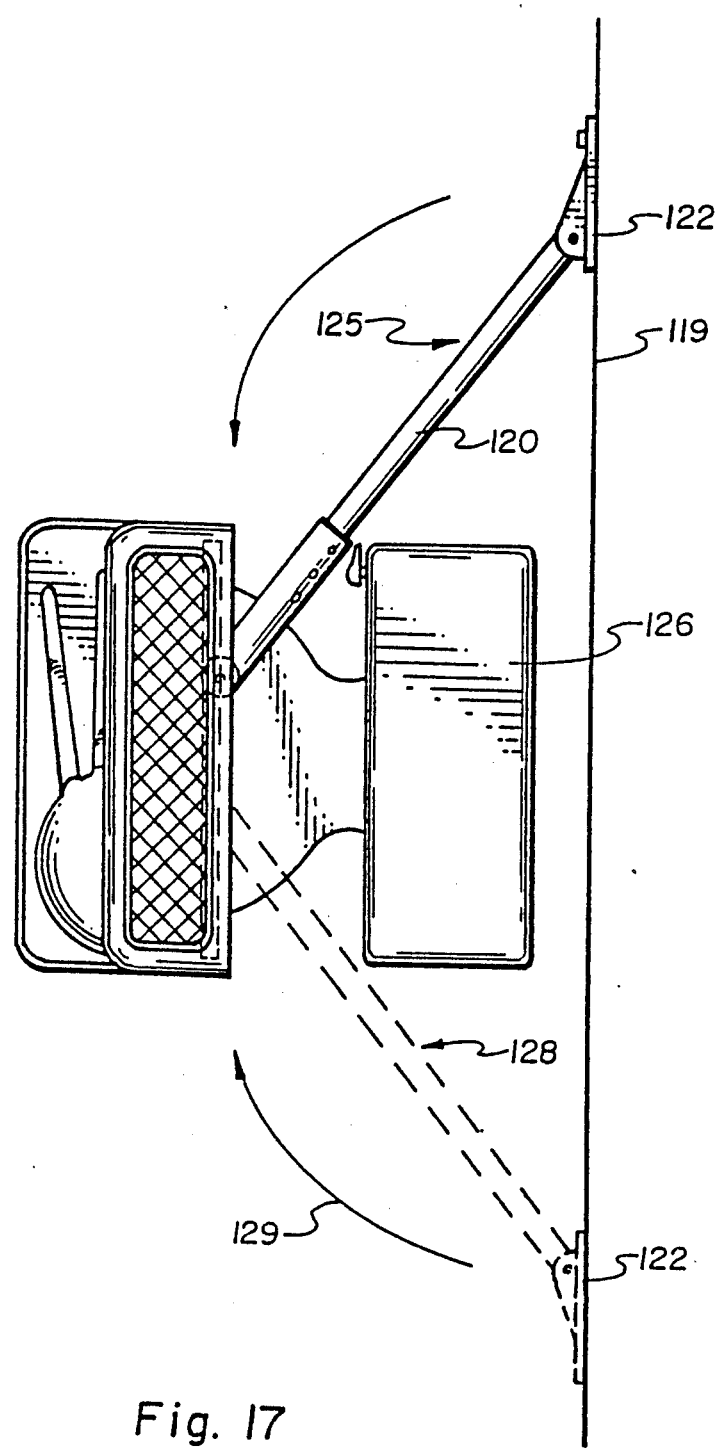
FIG. 17 is a top view of the cabinet illustrated as being mountable to a wall on either side of a toilet using adjustable arms.

FIGS. 15, 16 and 17 illustrate an alternative embodiment of the positioning means of the cabinet in which pressurized fluid cylinders 120 are pivotedly attached to the wall 47 at their first ends by plate mounts 122. The cylinders 120 are mounted to the back of the cabinet by mounts 124 on their opposing ends. The cabinet may be mounted either to the left side 125 of the toilet 126, as shown by FIG. 15, or to the right side 128 of the toilet 126. In this latter orientation, the cabinet swings in the direction 129, as shown in FIG. 17. As illustrated in FIG. 16, the cabinet 127 may be secured into position above the toilet 126 by means of adjustable clamps 130 of the type previously described which engage with the rim 132 of the toilet 126. In this embodiment, positioning is facilitated by means of two arms 134 pivotally connected at their midpoints 136. One end 138 of each cylinder is connected to the plate mount 122 near the point of attachment of rod 140 of the cylinder to the plate mount 122. The other end 142 of each arm is connected to the sleeve 144 of each cylinder.

Figure 18:
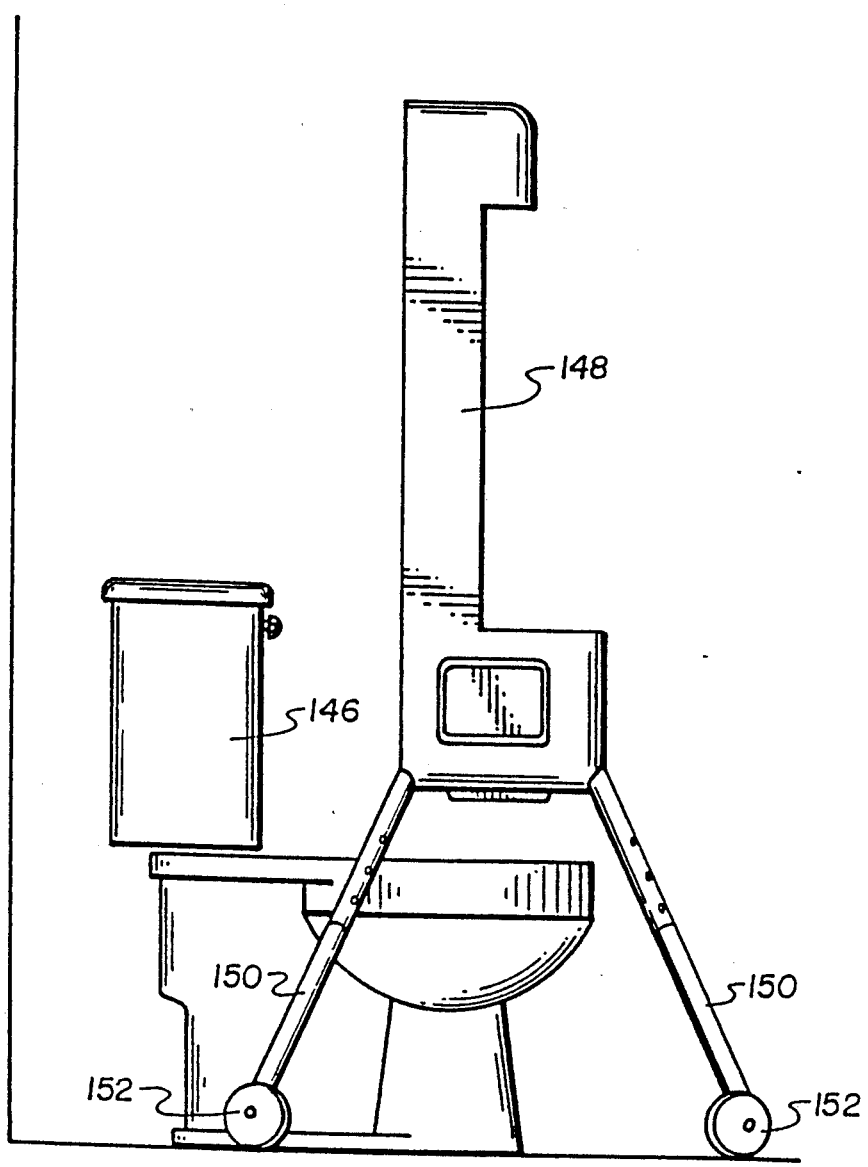
FIG. 18 is a side view of a cabinet mounted on legs with rollers.
Figure 19:
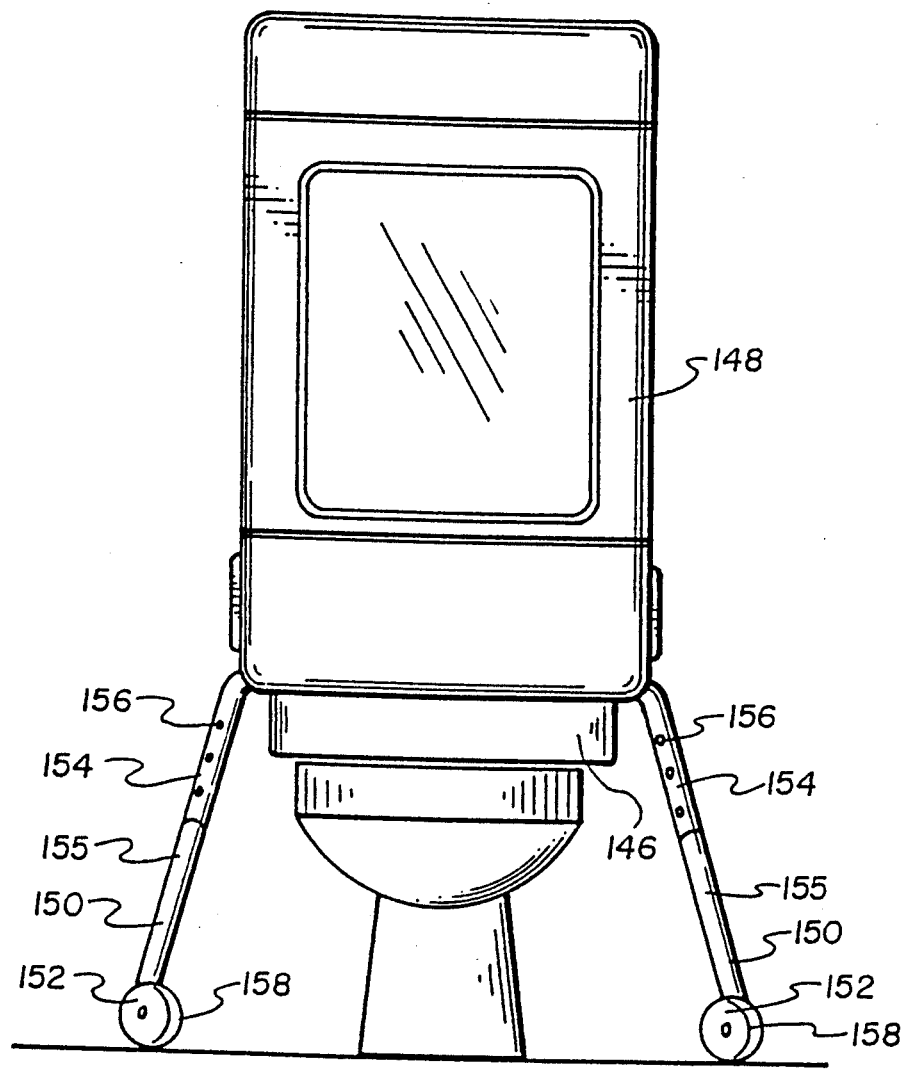
FIG. 19 is a front view of a cabinet mounted on legs with rollers.
Figure 20:
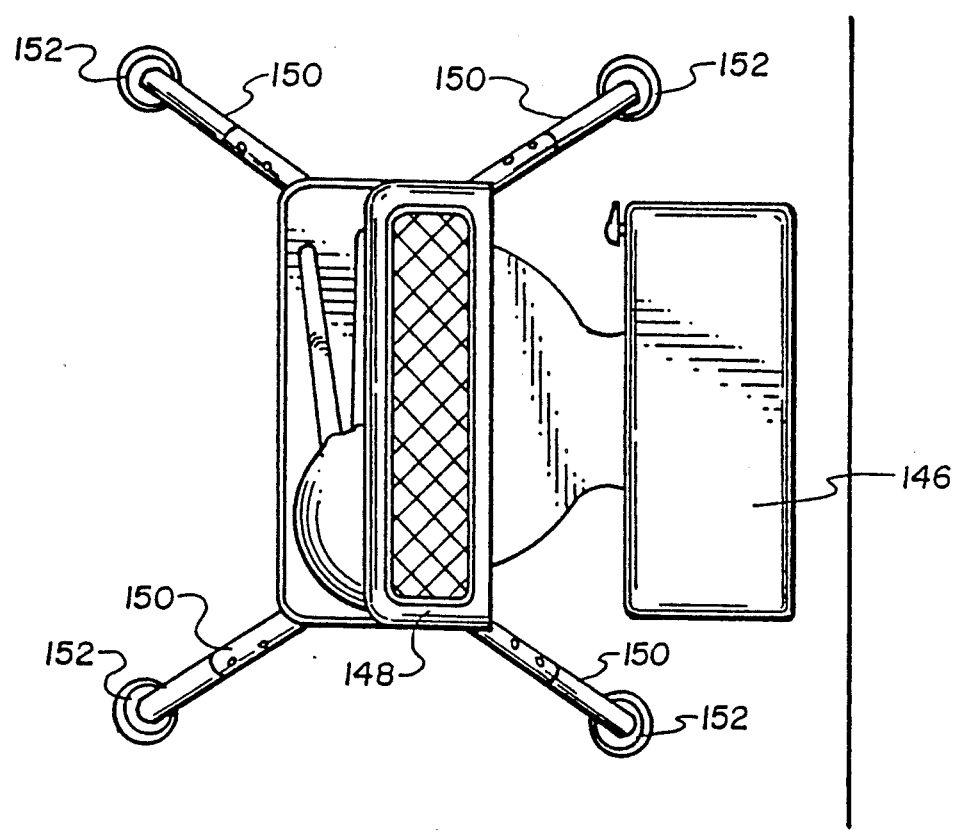
FIG. 20 is a top view of a cabinet mounted on legs with rollers.

FIGS. 18, 19 and 20 illustrate another alternative embodiment for moving the cabinet of the invention in close proximity to a toilet 146 in which the cabinet 148 is mounted to legs 150 which have rollers or wheels 152 rotatably secured at their lower ends. The legs of the invention can be adjusted in height by a conventional adjusting means, such as that illustrated in FIG. 19 where the legs are formed of two tubes 154 and 155, one being slidably disposed within the other. The relative position of the tubes to one another is determined by a conventional ball detent joint 156.

Once the cabinet has been rolled into position over the toilet, the unit can be locked into place by means of wheel locks or brakes 158, as shown in FIG. 19. As with the other positioning embodiments, the legged cabinet is positionable at a height appropriate for the user to view himself in the mirror, and is positioned at an optimum height for use of the countertop.

In a further embodiment of the invention illustrated in FIGS. 21-26, the station comprises two separatable units adapted for integral use.

Figure 21:
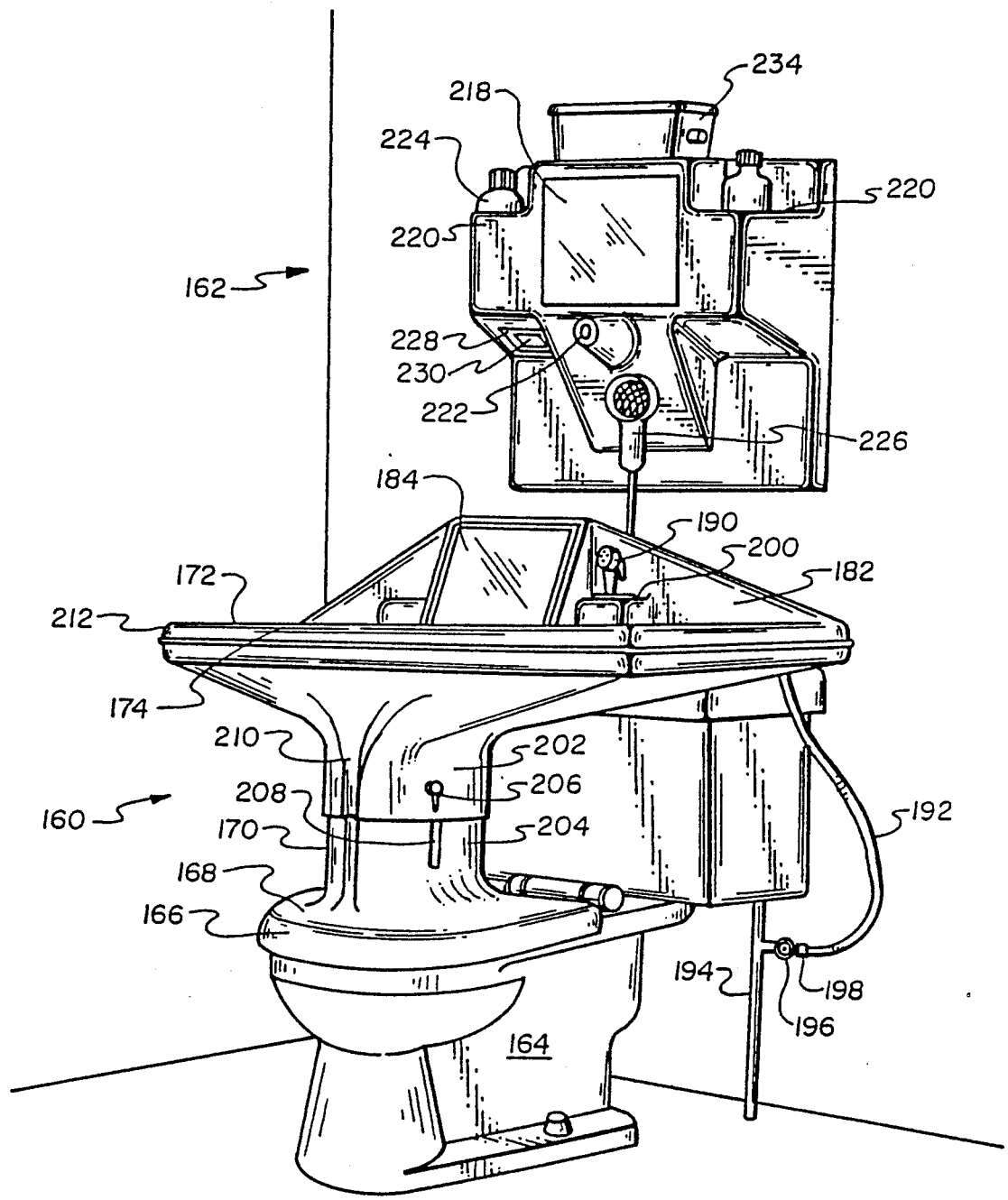
FIG. 21 is a perspective view of another embodiment of the station in accordance with the present invention.

As shown in FIG. 21, the station inoludes two fixtures, i.e., a lower cleaning fixture 160 and an upper wall-mounted cabinet fixture 162. The lower cleaning fixture 160 is designed to be detachable placed on a toilet bowl 164 during its use. Fixture 160 is not removable from the toilet but it is also portable so that it may be stored in a closet or elsewhere during periods of non-use. Thus, obvious ostomy bag cleaning apparatus is not visibly present in the bathroom except during cleaning operations.

The two fixtures are unique in that enhanced cleaning operations accrue from their simultaneous combined use.

The lower cleaning fixture 160 has a flange 166 at its lower extremity, which is configured to circumscribe the toilet bowl 164. Flange 166 curves downward at its periphery to enclose the lip of the toilet bowl. The flat portion 168 of flange 166 rests on the lip of the toilet bowl and supports the cleaning fixture 160, while the downward curving periphery accurately positions and holds the fixture in place. Optionally, a flexible gasket 161 may be juxtaposed between the flange and toilet bowl to further prevent movement of fixture 160, and to seal the interface and reduce the escape of odorous gases. Preferably, the gasket 161 is affixed to the underside of flange 66, and has a coefficient of friction which will prevent the lower fixture 160 from sliding on the toilet bowl. The flange 166 may be made in different sizes to accommodate the various lip sizes of toilet bowls in common use.

The lower fixture 160 includes a solid body 170 projecting upward from flange 166 to support countertop 172 and other apparatus useful to an ostomate for cleaning an ostomy bag. The features of the lower fixture 160 are more clearly shown by comparing FIGS. 21, 23 and 25. Generally horizontal countertop 172 has a rim 174 circumscribing its front and sides, and gradually slopes toward sink 176 which extends downward from an aperture 178 in the countertop.

Sink 176 drains into drainage conduit 180 which extends downward through body 170 to pass waste materials and fluid into toilet bowl 164.

Rigid rear wall 182 extends upwardly from the countertop 172 and supports mirror 184 located directly behind sink 178 and set at an angle 186 from the vertical. The user's line-of-sight 188 presents a full view of the front side of an ostomy bag and other components being cleaned on countertop 172. Angle 186 will depend upon the stature of the user and may vary from about 15° to 35°. Mirror 184 may be hinged or otherwise attached to rear wall 182, by means not shown, to be adjustable by the user.

The lower cleaning fixture 16 includes a flow-controllable spray head or nozzle 190 connected to a source of cleaning fluid, e.g., water, through extensible flexible hose 192. In the embodiment shown in FIG. 21, hose 192 is connected to toilet water supply line 194 through valve 196 and quick disconnect 198. Shelf 200 comprises a receptacle for the spray head 190 and includes an aperture 214 through which hose 192 may be passed. A sufficient length of hose 192 is coiled below shelf 200 for extending the spray head to the front corners 212 of the countertop, or further, enabling efficient and complete cleaning of the ostomy bag and associated equipment, as well as the countertop 172, sink 176 and drainage conduit 180, by the user.

Hose 192 may be comprised of several types of hose. A hose adapted for attachment to an extensible spray head may be normally stored under shelf 200, and a different hose type connected at one end to a water supply, and at its other end to the spray head hose.

Figure 23:
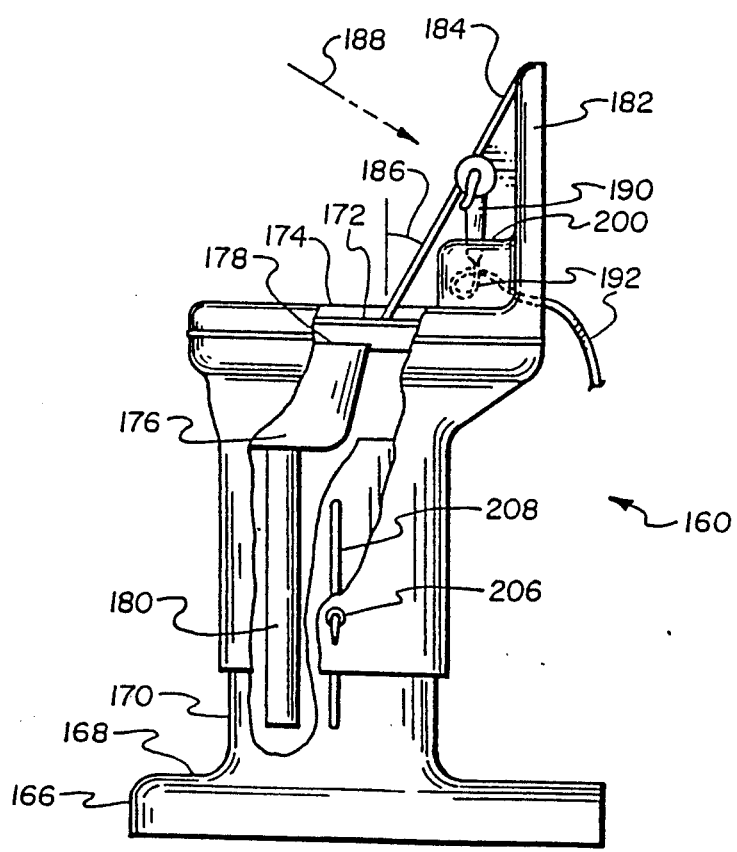
FIG. 23 is a partial cutaway side view of the lower cleaning unit of FIG. 21.
Figure 24:
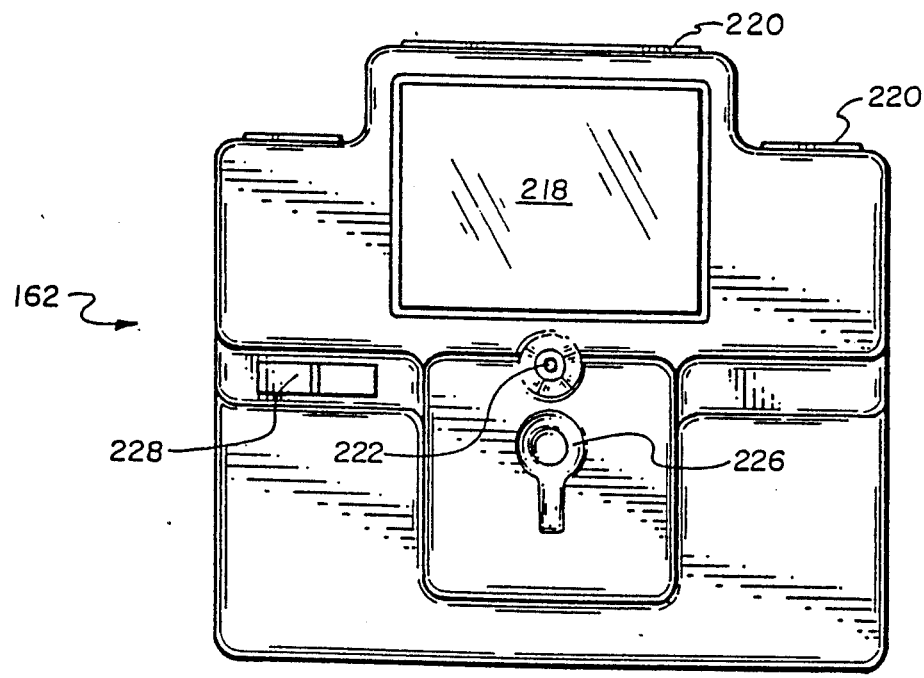
FIG. 24 is a top view of the lower cleaning unit of FIG. 21.
Figure 25:
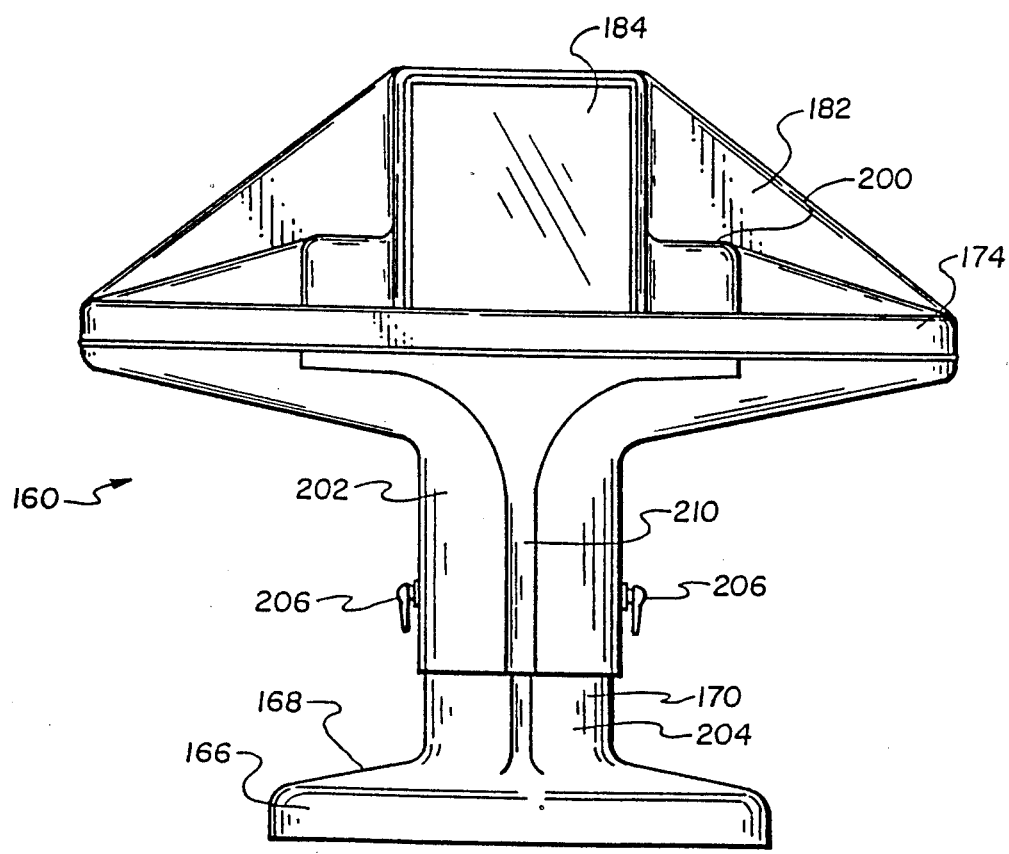
FIG. 25 is a front view of the lower unit of FIG. 21.

Body 170 may comprise a rigid, non-adjustable member connecting flange 166 with the countertop 172 and associated components. However, the preferred embodiment shown in FIGS. 21, 23 and 25 has a sleeved upper body section 202 flaring upwardly to countertop 172, and a sleeved lower body section 204 terminating in flange 166. Upper body section 202 is slightly larger in cross-section than lower body section 204, and fits slidingly over it. Thus, the upper and lower sections interfit so that the countertop 172 may be raised or lowered to a comfortable working position. One or more locks 206 enable the user to lock the lower and upper body sections at the desired position. The lock 206 may comprise a small clamp having an inner member which rides in a slot 208 in lower body section 204, as shown in FIGS. 21 and 23. Alternatively, the locks could be toggle operated pins which lock into holes in section 204.

Body 170 may be formed with a flared vertical rib 210 which makes the lower cleaning fixture 160 more rigid and prevents the upper and lower body sections from turning or twisting relative to each other.

Figure 26:
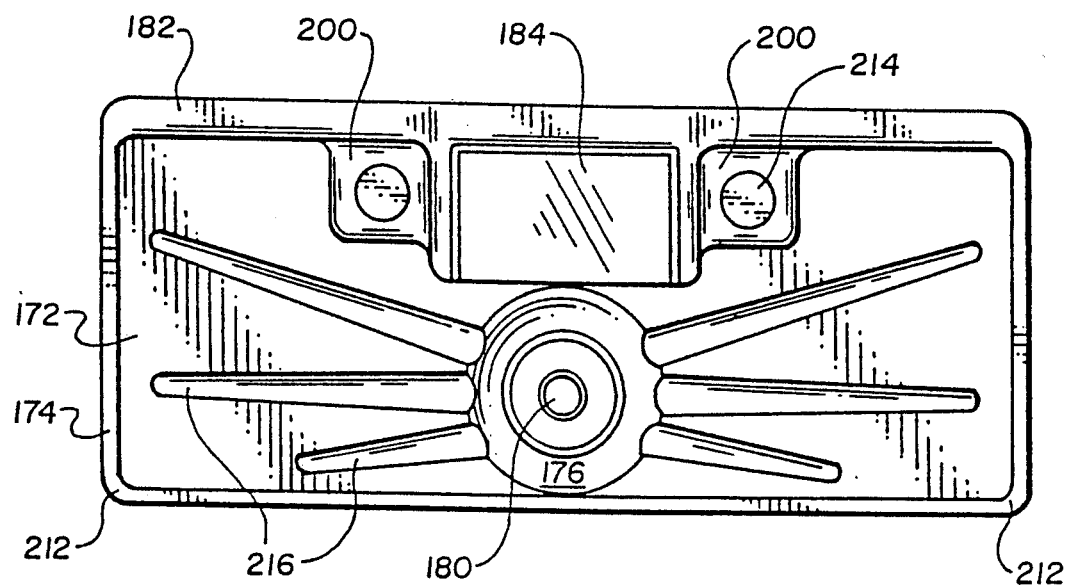
FIG. 26 is a top view of the lower cleaning unit of FIG. 21.

FIG. 26 is a top view of a lower cleaning fixture 160, showing countertop 172 with rim 174 and rear wall 182, mirror 184, and a pair of shelves 200 with apertures 214 for holding a spray head and other equipment, (not shown). Countertop 172 contains a multiplicity of drainage troughs 216 which empty into sink 176. Drainage conduit 180 in the bottom of sink 176 carries wastes and cleaning fluid into the toilet bowl.

If desired, one or more water outlets (not shown) may be provided in the upper periphery of sink 176, oriented to discharge at an angle non-radial with the center of the sink to provide a swirling motion. This aids in cleaning the sink.

The lower fixture 160 is preferably formed of a strong rigid plastic, by molding for example.

The upper cabinet fixture 162 is designed to be permanently wall mounted above a toilet and appear to be a standard bathroom fixture. It contains a vertically oriented mirror 218 on its front face, shelves 220 with receptacle 232 for holding bottles 224 of ostomy cleaning fluids or other supplies, lighting means 222, and other standard bathroom accessories such as a hair dryer 226 or shaver, not shown. An electrical outlet 228 provides power for these or other accessories, and may include a switch 230 for light 222.

Lighting means 222 may be a light bar which is extended outwardly to provide lighting for the cleaning operation.

Figure 22:
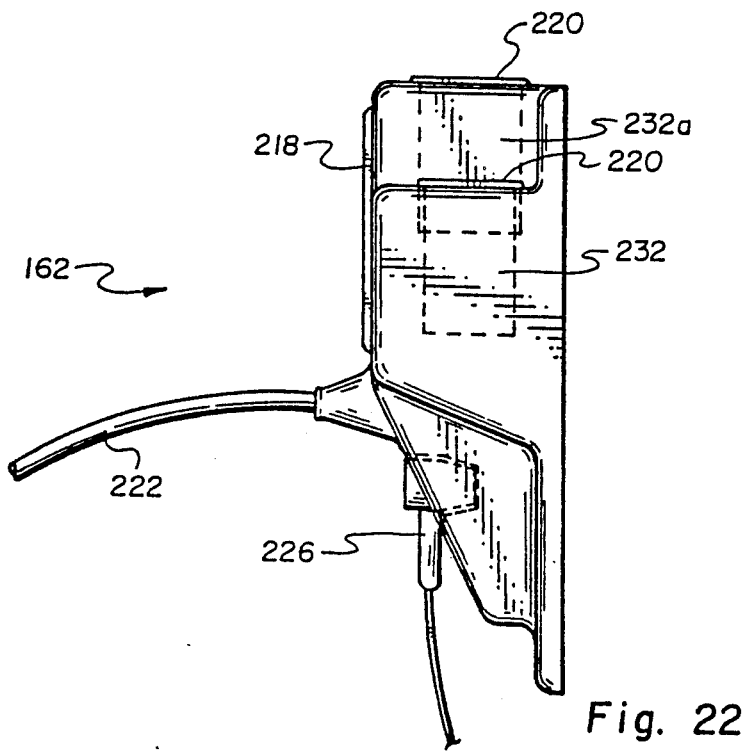
FIG. 22 is a side view of the upper cabinet unit of FIG. 21.

Uppermost receptacle a of FIG. 22 may house a container 234 of cleaning fluid with a hose, as shown in FIG. 21.

The apparatus of this embodiment provides means for cleaning an ostomy, ostomy bag and attendant components in a sanitary manner. Visual observation is enhanced by an integral light and mirror for viewing the front of the bag, not normally visible.

Only one connection, i.e., water, need be made for using the apparatus. The lower fixture 160 is lightweight and may be stored in a closet between uses.

Lower fixture 160 is adjustable in height to accommodate persons of differing stature.

Upper fixture has utility for both ostomy bag cleaning and such operations as hair drying or shaving. Thus, it is an unobtrusive fixture in the bathroom.

In summary, the various embodiments of this invention greatly enhance the regular cleaning operations the ostomate must attend to.

The various embodiments are intended to be illustrative of the inventive concept, and it will be obvious that numerous modifications may be made in the specific form and arrangement of components within the scope of the appended claims.

What is claimed is:

1. A station for use in storing, replacing and cleaning an ostomy bag and its associated equipment, comprising:

frame means;
    support means mounted on said frame means adapted for securing said frame means against a wall, said support means being adapted to extend laterally, wherein said frame means may be displaced outwardly from said wall to a location above a disposal location;
    a generally horizontal countertop mounted on said frame means adapted for a placement and retention of an ostomy bag thereon during cleaning of said ostomy bag, said countertop having a sink formed therein for draining liquid and waste materials from said ostomy bag and from said countertop; a mirror moujnted upright on said frame means;
    a light source mounted to said frame means for illuminating said countertop, a user and said mirror; and
    a drainage conduit, having a first end connected to said sink, said drainage conduit being adapted for carrying said waste materials and said liquid from said sink to said disposal location.

2. A station for use in storing, replacing a cleaning an ostomy bag and its associated equipment comprising:

frame means;
    support means mounted on said frame means adapted for securing said frame means against a wall, said support means being adapted to extend laterally, wherein said frame means may be extended outwardly from said wall to a location above a disposal location;
    a generally horizontal countertop mounted on said frame means adapted for a placement and retention of an ostomy bag thereon during a cleaning of said ostomy bag, said countertop having a sink formed therein for draining liquid and waste materials from said ostomy bag and from said countertop; and
    maceration means for macertaing said waste materials into a flushable form for disposal, said maceration means being mounted on said sink;
    a drainage conduit having a first end mounted on said maceration means, said maceration means being adapted for carrying said waste materials and said liquid from said sink to said disposal location.

3. A station for use in storing, replacing and cleaning an ostomy bag and its associated equipment, comprising:

frame means;
    support means mounted on said frame means adapted for securing said frame means against a wall, said support means being adapted to extend laterally, wherein said frame means may be extended outwardly from said wall to a location above a toilet;
    a generally horizontal countertop mounted on said frame means adapted for a placement and retention of an ostomy bag thereon during a cleaning of said ostomy bag, said countertop having a sink formed therein for draining liquid and waste materials from said ostomy bag and from said countertop;
    a drainage conduit, having a first end connected to said sink, said drainage conduit being adapted for carrying said waste materials and liquid from said sink to said toilet; and
    means for detachably securing said frame means to said toilet when said frame means is positioned above said toilet.

4. The station of claim 1 wherein said disposal location is a toilet.

5. A station for use in storing, replacing and cleaning an ostomy bag and its associated equipment, comprising:

frame means;
    support means mounted on sid frame means adapted for securing said frame means against a wall, said support means being adapted to extend laterally, wherein said frame means may be extended outwardly from said wall to a location above a toilet;
    a generally horizontal countertop mounted on said frame means adapted for a placement and retention of an ostomy bag thereon during a cleaning of said ostomy bag, said countertop having a sink formed therein for draining liquid and waste materials from said ostomy bag and from said countertop; and
    a drainage conduit, having a first end connected to said sink, said drainage conduit being adapted for carrying said waste materials and liquid from said sink to said toilet;
    wherein said frame means is fitted with securement means for engaging and forming a union with said toilet, and wherein said frame means is supported above said toilet.

6. The station of claim 1 further including a mirror for viewing a user's body, said mirror being positioned generally parallel to said user's body to enhance the user's view of an ostomy for removal, cleaning and replacement of said ostomy bag.

7. A station for use in storing, replacing and cleaning an ostomy bag and its associated equipment, comprising:

frame means;
    support means mounted on said frame means adapted for securing said frame means against a wall, said -support means being adpated to extend laterally, wherein said frame means may be extended outwardly from said wall to a location above a disposal location;

a generally horizontal countertop mounted on said frame means adapted for a placement and retention of an ostomy bag thereon during a cleaning of said ostomy bag, said countertop having a sink formed therein for draining liquid and waste materials from said ostomy bag and from said countertop;

a drainage conduit, having a first end connected to said sink, said drainage conduit being adapted for carrying said waste materials and said liquid from said sink to said disposal location;

a fluid-carrying flexible hose mounted on said frame means, said hose terminating in a controllable spray head for washing said ostomy bag and equipment, said hose being of a sufficient length for use in cleaning said ostomy bag and equipment and being retractable into said frame means and having a pressurized fluid source connected thereto.

8. A station for use in storing, replacing and cleaning an ostomy bag and its associated equipment, comprising:

a cabinet means for retaining an ostomy bag and its associated equipment therein, having:

support means mounted on said cabinet means adapted for securing said cabinet means against a wall, a mirror affixed to a back wall of said cabinet means and positioned generally parallel to a user's body to enhance said user's view of an ostomy during removal, cleaning and replacement of said ostomy bag, a generally horizontal countertop mounted on said cabinet means and oriented in front of and below said mirror, having a sink formed therein for draining liquid and waste materials from said ostomy bag and from said countertop, a fluid-carrying flexible hose, mounted on said cabinet means, terminating in a flow-controllable spray head for washing said ostomy bag and equipment, said hose being of a sufficient length for use in cleaning said ostomy bag and equipment and said hose being retractable into said cabinet means having a pressurized fluid source connected thereto, and a drainage conduit mounted on said sink for carrying said waste materials and liquid from said sink to a disposal location.

9. The station of claim 8 wherein said disposal location is a toilet.

10. The station of claim 9 wherein said cabinet means is fitted with securement emans for engaging and forming a union with said toilet, wherein said cabinet means is supported above said toilet.

11. The station of claim 10, wherein said securement means is adapted to be adjustable to form a union with rims of toilets of various dimensions.

12. The station according to claim 9, wherein said cabinet means includes a hinged door having a shelf adapted to scrape a surface of said countertop upon a closing of said door.

13. The station according to claim 12, wherein said support means includes at least one pressurized fluid cylinder, said support means being adapted for displacing said cabinet means outward from said wall into a position over and above said disposal location.

14. The station according to claim 4, wherein said support means comprises a plurality of legs, each leg having a first end mounted to the bottom of said cabinet means and a second end attached to a wheel, said cabinet means thereby being moveable and positionable over said toilet.

15. The station of claim 14, wherein said legs are adjustable in length to adjust the height of said cabinet means.

16. A station for replacing and cleaning on ostomy bag and equipment components, and for storage of same, comprising:

a lower cleaning fixture adapted to be supportably positioned on, and circumscribing a toilet bowl, said lower cleaning fixture having a water supply and a body extending upwardly to a generally horizontal countertop;

said countertop having a sink formed therein, said countertop being slightly sloped downwardly toward said sink to drain therein;

said lower cleaning fixture including a rigid rear wall extending upwardly from said countertop and encompassing therein a controllable water spray head mounted on an extensible flexible water hose connected to a water supply, and a mirror for a user to view said cleaning of ostomy and ostomy bag;

said lower cleaning fixture being adapted to be hand-lifted from said toilet bowl and removed for storage; and an upper cabinet fixture adapted to be mounted on a wall above said toilet bowl, and including a generally vertically oriented mirror, lighting means for illuminating said countertop, user, and ostomy bag, and at least one shelf for storing said equipment components.

17. The station according to claim 16, wherein said lower cleaning fixture includes a flanged lower terminus which supportably rests on said toilet bowl, and circumscribes same.

18. The station according to claim 17, further comprising a flexible gasket between said flanged lower terminus and said toilet bowl, for sealingly mounting said lower cleaning fixture.

19. The station according to claim 16, wherein said lower cleaning fixture comprisess interfitting sleeved upper and lower body sections for slidably adjusting the height of said lower cleaning fixture above said toilet bowl, and an integral lock for maintaining said height.

20. The station according to claim 16, wherein said lighting means comprises an extensible light bar which is retractable into said upper cabinet fixture.

21. The station according to claim 16, wherein said upper cabinet fixture includes a mount for storing a hair dryer, and an electrical outlet for providing electrical power thereto.

* * * * *